(12) United States Patent
Kanzaki et al.

(10) Patent No.: US 7,483,128 B2
(45) Date of Patent: Jan. 27, 2009

(54) FOREIGN MATTER INSPECTION APPARATUS AND METHOD

(75) Inventors: Toyoki Kanzaki, Kyoto (JP); Shu Yoshinaga, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/155,991

(22) Filed: Jun. 17, 2005

(65) Prior Publication Data

US 2006/0001864 A1    Jan. 5, 2006

(30) Foreign Application Priority Data

Jun. 18, 2004    (JP)    ............... 2004-180577

(51) Int. Cl.
*G01N 21/00* (2006.01)
(52) U.S. Cl. ............... 356/237.2; 356/237.4
(58) Field of Classification Search ........ 356/369, 356/237.1–237
See application file for complete search history.

(56) References Cited

U.S. PATENT DOCUMENTS 5,796,475 A * 8/1998 Kanzaki et al. .......... 356/239.4
5,936,726 A * 8/1999 Takeda et al. ............ 356/237.2

FOREIGN PATENT DOCUMENTS

| EP | 0335163 A2 * | 4/1989 |
| JP | 01-245136 | 9/1989 |
| JP | 09-218163 | 8/1997 |

* cited by examiner

*Primary Examiner*—Tarifur Chowdhury
*Assistant Examiner*—Tara S Pajoohi (57) ABSTRACT

An apparatus for inspecting foreign matter on substrates on which circuit patterns, such as reticles or masks, are formed, reduces false detection due to scattered/diffracted light from circuit patterns and also reduces the occurrence of undetected foreign matters. A light source such as a scanning laser beam having a certain polarization angle to the surface of an inspection object substrate is provided. A main detector extinguishes scattered/diffracted light caused by a circuit pattern formed on the surface of the inspection substrate and detects an output signal. A reference detector transmits scattered/diffracted light caused by the circuit pattern, and detects an output signal. A signal processor calculates a difference signal by subtracting the intensity of a polarization component detected by the reference detector from the intensity of a polarization component detected by the main detector, and discriminates a signal with a large width caused by the circuit pattern and a signal with an acute peak caused by foreign matter.

15 Claims, 9 Drawing Sheets

FOREIGN MATTER INSPECTION APPARATUS AND METHOD

BACKGROUND OF THE INVENTION

1. Field of the Invention

The present invention relates to an inspection device and method for inspecting foreign matters on reticles or masks used for printing circuit patterns on semiconductor wafers in an LSI production process, for example, on planar substrates such as semiconductor wafers on which circuit patterns are formed.

2. Description of Related Art

In inspecting foreign matters on the surface of reticles or masks, circuit patterns themselves have been increasingly falsely detected as foreign matter, since the recent circuit patterns being formed on the reticles or masks have become highly integrated and miniaturized along with a high integration of LSIs and the like. In order to prevent such kind of false detection as mentioned above, many improvements of apparatus, for example, a use of polarized light, a change in arrangement of a detector, and arranging a spatial filter in front of the detector, have been conventionally taken.

Japanese Laid-Open Patent Application No. 1-245136 describes a foreign matter inspection apparatus including a laser beam source for irradiating, while scanning, a laser beam having a certain polarization angle onto the surface of an inspection substrate; an analyzer for transmitting polarization components of two different polarization angles of scattered/diffracted light generated on the surface of the inspection substrate along with emission of the laser beam; and a detection device having two detectors (a main detector and a reference detector), each of which is configured to be capable of detecting intensity thereof. The inspection apparatus determines the existence of foreign matter by means of a method called a polarization differential method, in which the intensities of the polarization components of two different polarization angles detected by the two detectors respectively are compared, and the ratio and/or the sign of the difference between them are determined to thereby determine whether foreign matter exists or not.

Figure 10:
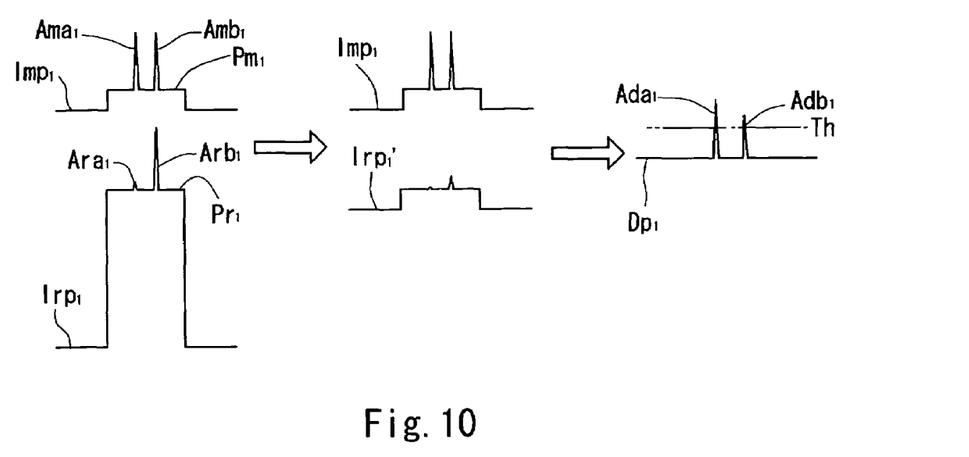
FIG. 10 is a diagram for explaining a conventional polarization differential method.

FIG. 10 is an illustration of signal waveforms for explaining an example of signal processing using a polarization differential method. In FIG. 10, $Imp_1$ indicates an intensity signal of a polarization component of a certain polarization angle to the surface of an inspection substrate (hereinafter referred to as an M polarization component), and $Irp_1$ indicates an intensity signal of a polarization component of a different polarization angle from the aforementioned angle to the surface of the inspection substrate (for example, orthogonal to the M polarization component, hereinafter referred to as an R polarization component). $Ama_1$, $Amb_1$, $Ara_1$, and $Arb_1$ indicate representative signals caused by foreign matter, and $Pm_1$ and $Pr_1$ indicate signals caused by circuit patterns formed on the inspection substrate.

As shown in FIG. 10, a signal $Pr_1$ caused by a circuit pattern is detected at an extremely high level, and a signal $Pm_1$ caused by the same circuit pattern is detected at a low level. On the other hand, as for signals $Ama_1$ and $Ara_1$ caused by foreign matter, the signal $Ara_1$ tends to be detected at a lower level than the signal $Ama_1$, and for signals $Amb_1$ and $Arb_1$ caused by another foreign matter, both signals $Amb_1$ and $Arb_1$ are detected at a similar level.

Accordingly, the gain of the intensity signal $Irp_1$ is adjusted so as to make the signal $Pr_1$ of the R polarization component and the signal $Pm_1$ of the M polarization component approach a similar level, and the difference $Dp_1$ between the signal $Irp_1'$ and $Imp_1$ is calculated. When the difference $Dp_1$ is not more than a predetermined threshold level Th, the signal $Imp_1$ is removed as noise, and if the difference $Dp_1$ exceeds the threshold value Th, the signal $Imp_1$ is outputted as foreign matter signals $Ada_1$ and $Adb_1$. In general, the signal $Pr_1$ caused by a circuit pattern is sufficiently large comparing with the signal $Pm_1$, whereby it is desirable to set a gain of the intensity signal $Irp_1$ to $\frac{1}{10}$ to $\frac{1}{100}$ times the gain of the intensity signal $Imp_1$.

Japanese Laid-Open Patent Application No. 9-218163 shows an apparatus in which a first signal processing line with lowpass characteristics and a second signal processing line without lowpass characteristics are provided in parallel with each other on the output side of a detector, and the difference between outputs from these two signal processing lines is calculated, whereby scattered/diffracted light from a circuit pattern is discriminated from scattered/diffracted light from foreign matter (hereinafter, this discriminating method is called a method using a lowpass difference).

That is, in the method using a lowpass difference, signals caused by a circuit pattern are formed such that a high frequency signal is superposed on a trapezoidal or rectangle (low frequency) signal. Therefore, this signal is branched into two systems, and one is inputted into a circuit with lowpass characteristics and the other is inputted into a circuit with delay characteristics so as to delay the signal through the circuit with lowpass characteristics to thereby synchronize both signals. Then, the difference between the signals is calculated, whereby it is possible to detect only a signal with a high frequency caused by foreign matter.

However, in the case of using the polarization differential method as described in Japanese Laid-Open Patent Application No. 1-245136, since polarization characteristics were used, it is not a sufficiently effective means in the case of, for example, a circuit pattern configuration in which scattered/diffracted light from the circuit pattern causes multiple diffraction/scattering effects.

Figure 11:
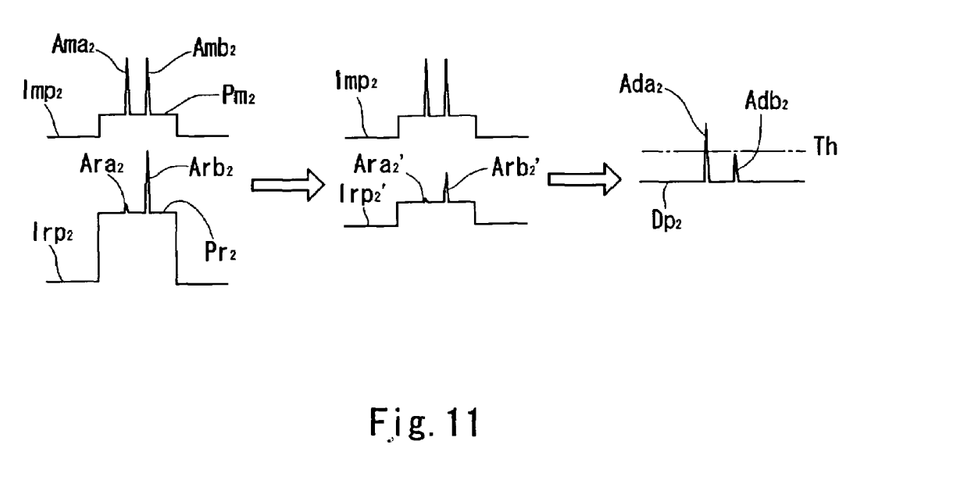
FIG. 11 is a diagram showing a problem in the conventional polarization differential method.

FIG. 11 is an illustration of signal waveforms for explaining another example of performing signal processing, using the polarization differential method, on signals from a surface of an inspection object which may cause multiple diffractions and multiple scattering. $Imp_2$ indicates an intensity signal of the M polarization component, and $Irp_2$ indicates an intensity signal of the R polarization component. Further, $Ama_2$, $Amb_2$, $Ara_2$ and $Arb_2$ are signals caused by scattered/diffracted light due to foreign matter existing on the inspection object, and $Pm_2$ and $Pr_2$ are signals caused by a circuit pattern formed on the inspection object.

As shown in FIG. 11, when scattered/diffracted light from a circuit pattern causes multiple diffraction/scattering, the signal $Pr_2$ caused by the circuit pattern is detected at a higher level than the signal $Pm_2$. However, the difference between them is not large enough as that of the example shown in FIG. 10. Therefore, even when the signals $Ama_2$, $Ara_2$, $Amb_2$ and $Arb_2$, caused by foreign matter, are detected at the similar level to those of FIG. 10, the signals $Ara_2$ and $Arb_2$ caused by foreign matter become larger comparing with the signal $Pr_2$ caused by the circuit pattern.

Thus, when the level of the signal $Pr_2$ caused by the circuit pattern is adapted to the level of the signal $Pm_2$ as shown with the reference numeral $Irp_2'$, the signals $Ara_2'$ and $Arb_2'$ caused by foreign matter reside somewhat. Therefore, in the difference $Dp_2$ between both signals $Irp_2$ and $Imp_2$, if the signals $Ada_2$ and $Adb_2$ caused by foreign matter become small so as to be not more than the threshold value Th, they are incorrectly determined as noise signals and removed. In other words, there has been a possibility that the signal $Adb_2$, caused by foreign matter scattering relatively strong light even in the polarization differential method, becomes so small that foreign matter is missed.

Figure 12A:
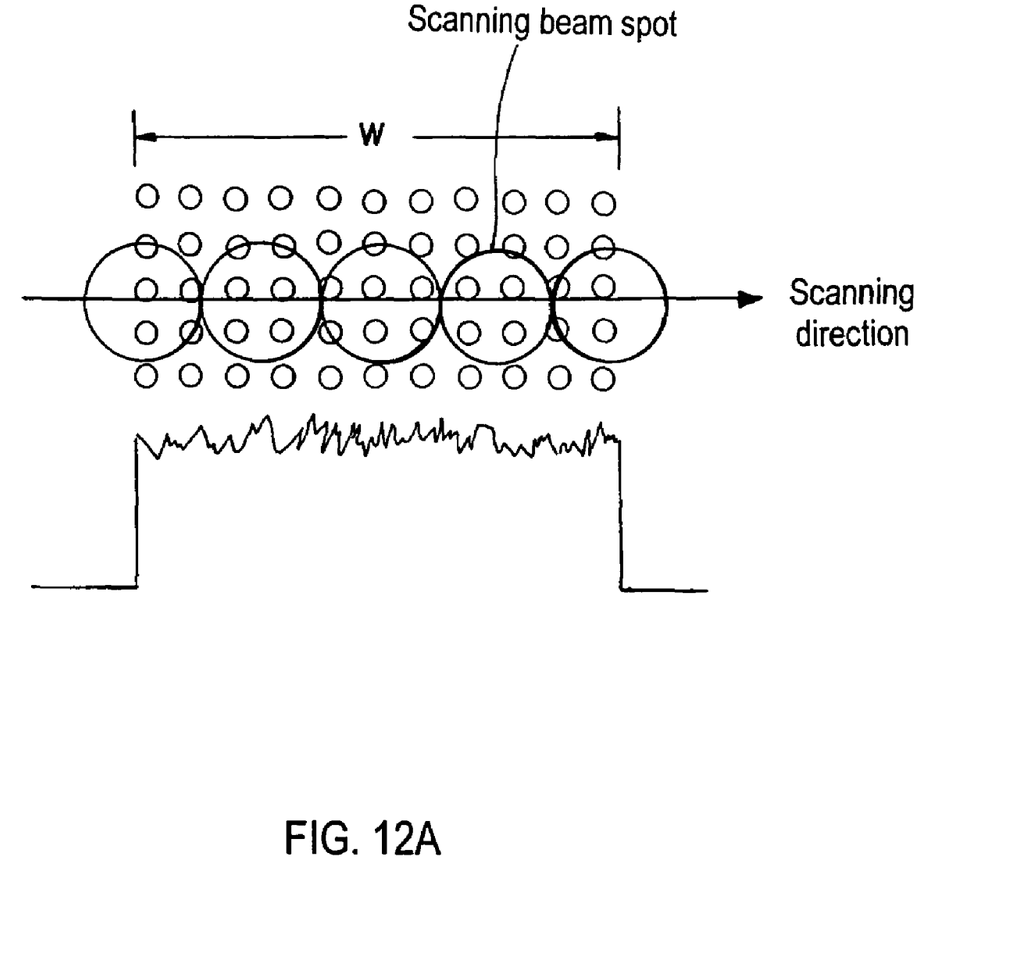
FIGS. 12(A) and 12(B) are illustrations showing a problem in a conventional method of calculating a low-pass difference.
Figure 12B:
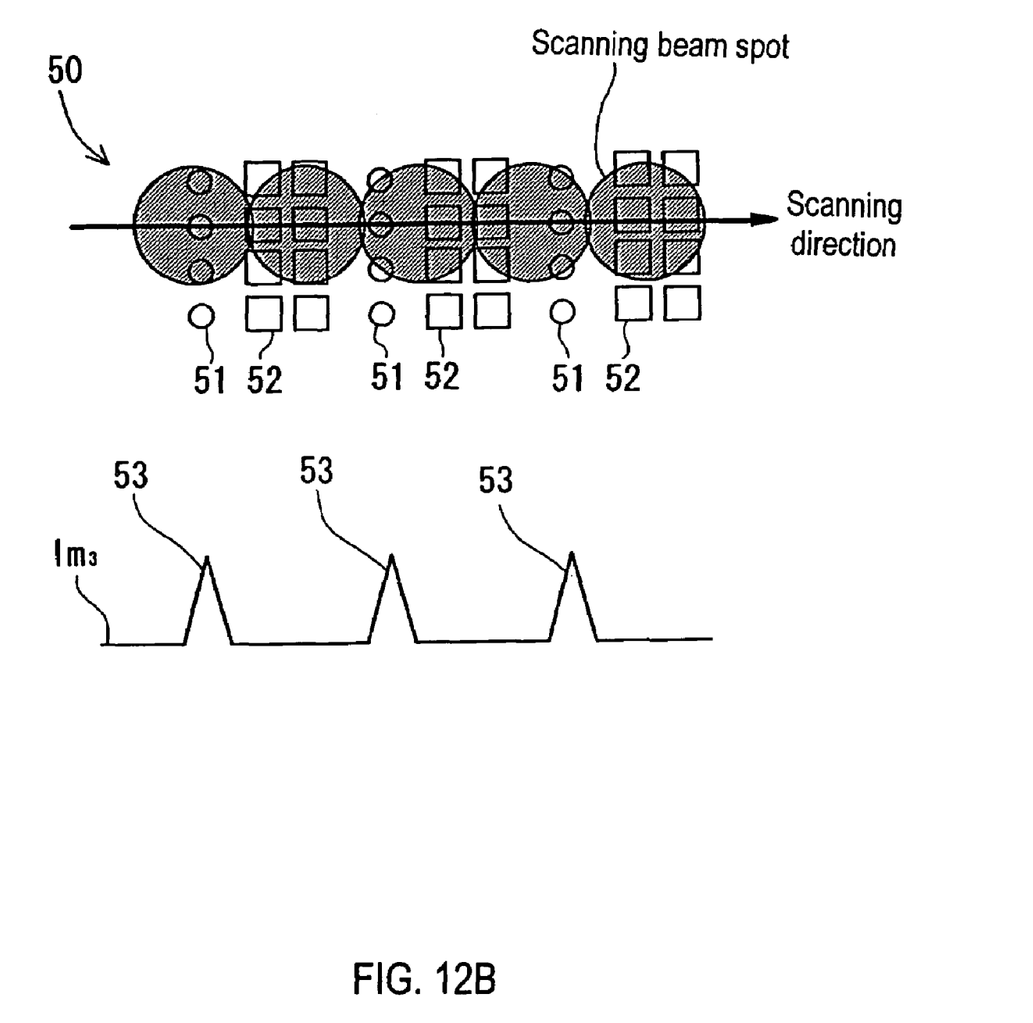

Further, there are signal forms according to pattern alignment shown in FIGS. 12(A) and 12(B). In the case of performing signal processing using the lowpass difference as shown in Japanese Laid-Open Patent Application No. 9-218163, the effect is low for a circuit pattern structure of a non-dense arrangement shown in FIG. 12(B), whereby it has not been sufficiently effective for all of the various circuit patterns that may be tested.

FIG. 12(A) shows the signal from dense patterns. When plotting the time along the horizontal axis and the signal intensity along the vertical axis, the signal from the fine patterns comprises a rectangular form. On the other hand, the signal from non-dense aligned patterns or particles exists independently, showing the sharp signal plot as shown in FIG. 12(B). $Im_3$ indicates an exemplary signal detected when the inspection object substrate is inspected. As shown in FIG. 12(B), the inspection object substrate 50 includes a circuit pattern 51 easily shining with a laser beam, and a circuit pattern 52 that is not easily shining.

When the inspection object substrate 50, in which the easily shining circuit patterns 51 are distributed in a non-dense manner, is inspected, locally acute signals 53 caused by the circuit patterns 51 are detected as shown in FIG. 12(B). Even though signal processing using a lowpass difference is applied to such signals 53, it is still difficult to remove these signals 53, whereby there is a possibility to detect them as erroneously caused by foreign matter.

Further, even in a case of a relatively large circuit pattern being formed, a leading edge of a signal caused by the circuit pattern includes a component with high frequency, whereby there may be a case where it is not removed completely by signal processing using the lowpass difference. Therefore, there has been a possibility that the leading edge of a signal caused by the circuit pattern is detected as foreign matter in error. Consequently, it is required to increase the upper limit of frequency to be cut by the signal processing using a lowpass difference, which may cause the inspection to miss foreign matter.

The present invention has been developed in view of the aforementioned matters.

SUMMARY OF THE INVENTION

An object of the present invention is, in inspecting foreign matters on substrates on which circuit patterns, such as reticles or masks, are formed, to provide a foreign matter inspection apparatus and a foreign matter inspecting method capable of reducing false detection due to scattered/diffracted light from circuit patterns and also reducing the occurrence of missed foreign matters.

In order to achieve the aforementioned object, a foreign matter inspection apparatus includes a light source for irradiating, while scanning, a laser beam having a certain polarization angle to the surface of an inspection object substrate; a main detector which has an optical means for extinguishing scattered/diffracted light caused by a circuit pattern formed on the surface of the inspection object substrate among scattered/diffracted light generated on the surface of the inspection object substrate along with irradiation of the laser beam, and detects an output signal from the optical means; a reference detector which has an optical means for transmitting scattered/diffracted light caused by the circuit pattern, and detects an output signal from the optical means; and a signal processor for calculating a difference signal by subtracting the intensity of R a polarization component detected by the reference detector from the intensity of M a polarization component detected by the main detector, and discriminating to provide an output signal with widely distributed pattern caused by the circuit pattern and a signal with an acute peak caused by foreign matter, included in the difference signal (M−R), by their frequencies.

The device may include a condenser lens for condensing the scattered/diffracted light; a half mirror for splitting the scattered/diffracted light condensed by the condenser lens into two optical paths; and analyzers inserted in the respective optical paths, and the main detector and the reference detector may be arranged at the ends of respective optical paths split by the half mirror.

A foreign matter inspecting method comprises the steps of irradiating, while scanning at a predetermined velocity v [mm/sec] a laser beam having a certain polarization angle to the surface of the inspection object substrate; detecting an output signal of an optical unit for extinguishing scattered/diffracted light caused by a circuit pattern formed on the surface of the inspection object substrate among scattered/diffracted light generated on the surface of the inspection object substrate along with irradiation of the laser beam, and an output signal of an optical unit for transmitting the scattered/diffracted light caused by the circuit pattern; calculating a difference signal by subtracting the output signal of the optical unit for transmitting the scattered/diffracted light caused by the circuit pattern from the output signal of the optical unit for extinguishing the scattered/diffracted light caused by the circuit pattern; and discriminating and taking out a signal with widely distributed pattern caused by the circuit pattern and a signal with an acute peak caused by foreign matter, included in the difference signal, by their frequencies.

The foreign matter inspecting method may include the steps of condensing the scattered/diffracted light; splitting the condensed light into two optical paths by the half mirror; by arranging, on one of the split optical paths, an analyzer transmitting a polarization component of a polarization angle for extinguishing the scattered/diffracted light caused by the circuit pattern, detecting the intensity of the polarization component; and by arranging, on the other optical path, an analyzer transmitting a polarization component of a polarization angle for transmitting the scattered/diffracted light caused by the circuit pattern, and detecting the intensity of the polarization component.

In the above foreign matter inspecting apparatus and method, an interval T (see FIG. 12(A)) of the signal caused by the circuit pattern equals a distribution width W (see FIG. 12(A)) of the circuit pattern per scanning velocity v of the laser beam.

In a case of an inspection object substrate on which circuit patterns are arranged at non-dense intervals, for example, signals caused by the circuit patterns can be lowered substantially by using the polarization differential method, whereby the signals can be clearly discriminated from signals caused by foreign matter. Further, in a case of a circuit pattern with which multiple reflections and multiple diffractions are made incident on a detector, trapezoidal signals with low frequencies can be removed through signal processing using a lowpass difference in the latter stage. Accordingly, there is no need to remove signals caused by the circuit pattern completely by the polarization differential method. Therefore, it is possible to detect foreign matter with high sensitivity by performing subtraction processing of the polarization differential method to the extent of not damaging the sensitivity of foreign matter signals included in the difference signal.

Additionally, in a case of an inspection object substrate where multiple reflections and multiple diffractions are caused, a light emitting point becomes larger than the original spot at which the laser beam is irradiated, which generates corrupted signals, somewhat obtuse (signals including low frequency $$f_L\left(=\frac{1}{2T}\right),$$

comparing with signals of scattered light and diffracted light which are made incident directly. Therefore, an inspection object substrate generating multiple reflections and multiple diffractions is suitable for signal processing using a lowpass difference, so it is possible to remove signals caused by circuit patterns by the signal processing using a lowpass difference.

Further, when measuring an inspection object substrate having circuit patterns which are less effective in both signal processing using the polarization differential method and a lowpass difference, that is, when inspecting an inspection object substrate on which circuit patterns arranged in a non-dense manner are formed and which causes multiple reflections, signal levels caused by the circuit patterns are lowered by the polarization differential method, and an effect of the lowpass difference can be achieved as well, though each effect is small. Therefore, it is possible to remove signals caused by the circuit patterns effectively. That is, a combination of signal processing using the polarization differential method and a lowpass difference is important for lowering the signal level caused by the circuit patterns as well as detecting foreign matter reliably.

The foreign matter inspection apparatus of the present invention is capable of reducing false detection due to circuit patterns for samples having various circuit pattern configurations, from a non-dense and rough circuit pattern configuration to a dense and fine circuit pattern configuration, and further, it is capable of detecting foreign matter without missing it.

In the case where a condenser lens for condensing the scattered/diffracted light, a half mirror for splitting the scattered/diffracted light condensed by the condenser lens into two optical paths, and analyzers inserted in the respective optical paths are provided, and the main detector and the reference detector are arranged at the ends of respective optical paths split by the half mirror, it is possible to put together luminous flux of scattered/diffracted light which is the inspection object to be inspected by the main detector and the reference detector, whereby more precise measurement can be performed. Therefore, even when inspecting an inspection object substrate which scatters light with different distribution depending on angle, it is possible to discriminate foreign matter accurately.

In the foreign matter inspecting method, the level of signals caused by circuit patterns can be lowered effectively by combining the polarization differential method and signal processing using a lowpass difference even in an inspection object substrate on which circuit patterns are arranged at non-dense intervals, in an inspection object substrate which causes multiple reflections and multiple diffractions, or in an inspection object substrate which causes multiple reflections and multiple diffractions and on which circuit patterns are arranged at non-dense intervals. Therefore, it is possible to detect signals caused by foreign matter with high sensitivity.

In the case of condensing the scattered/diffracted light, splitting the condensed light into two optical paths by the half mirror, arranging on one of the split optical paths, an analyzer transmitting a polarization component of a polarization angle for extinguishing the scattered/diffracted light caused by the circuit pattern so as to detect the intensity of the polarization component, and arranging, on the other optical path, an analyzer transmitting a polarization component of a polarization angle for transmitting the scattered/diffracted light caused by the circuit pattern so as to detect the intensity of the polarization component. Foreign matters can be discriminated accurately even when inspecting an inspection object substrate which scatters light with different distribution depending on angles, by putting together the luminous flux of scattered/diffracted light which is the inspection object to be inspected by the main detector and the reference detector.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

Figure 1:
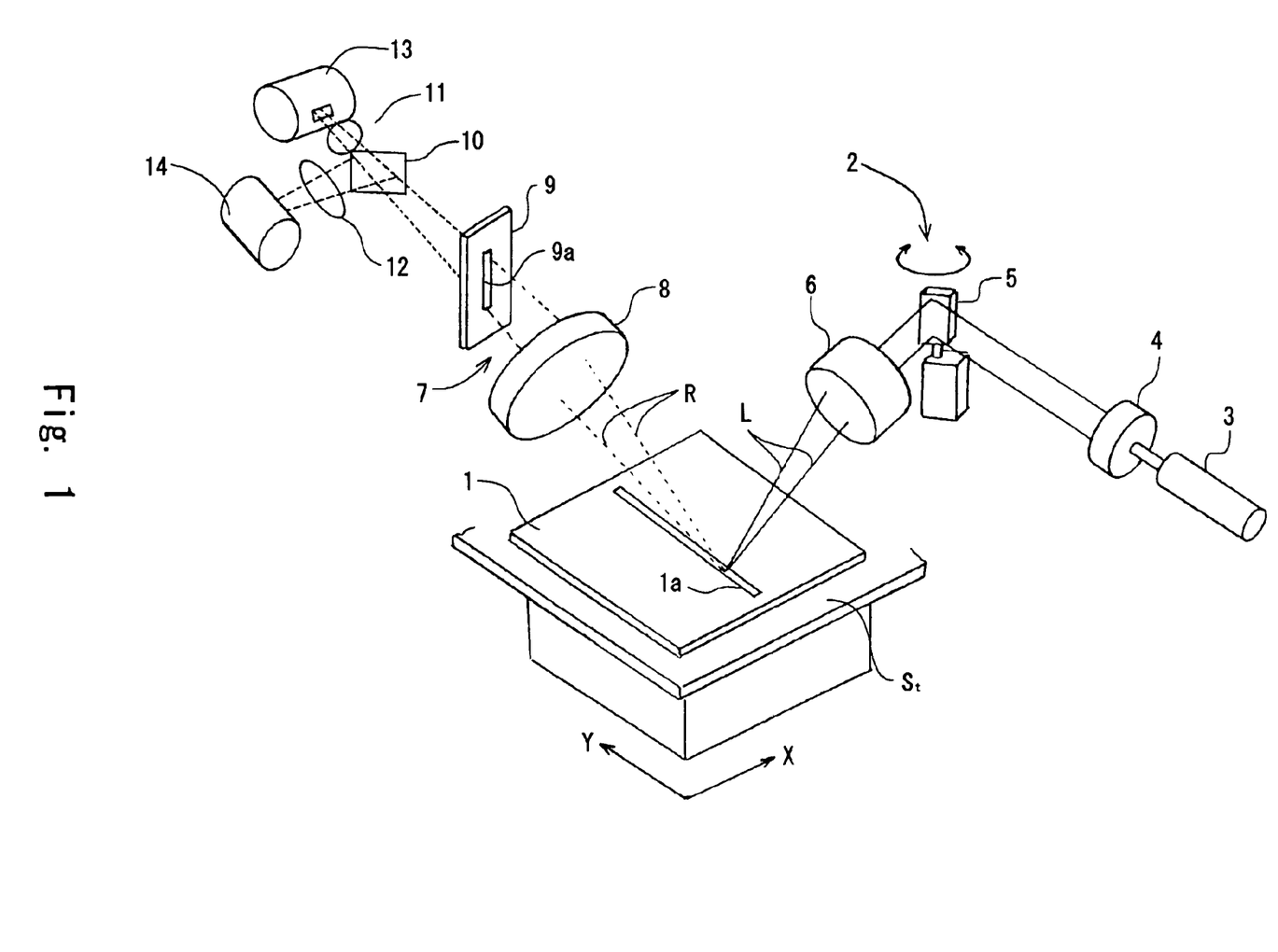
FIG. 1 is a perspective view showing a schematic configuration of an exemplary substrate inspection device according to the present invention.

FIG. 1 shows a typical hardware configuration of a foreign matter inspection device. In FIG. 1, reference numeral 1 indicates an inspection object substrate (such as a reticle) on which a circuit pattern (not shown) is formed, and is placed horizontally on an inspection stage St. The inspection stage St is set to be movable slidingly in the arrow X direction and in the arrow Y direction orthogonal to the arrow X direction, respectively.

Reference numeral 2 indicates a light source (incident optical system) for irradiating, while scanning, a laser beam L linearly on the surface of the inspection object substrate 1 (hereinafter referred to as a sample) in the arrow Y direction. The light source 2 includes, for example, an He—Ne laser oscillator 3 emitting a laser beam L of a certain polarization angle, a beam expander 4, a galvanometer mirror 5, and a condenser lens 6. The light source 2 is so configured that the laser beam L from the laser oscillator 3 is irradiated at a predetermined prescribed angle from above the sample 1 while reciprocally and linearly scanning within a predetermined prescribed range in the Y direction.

Reference numeral 7 indicates a detecting optical system for detecting scattered/diffracted light R from the irradiated surface of the laser beam L irradiated to the sample 1. The detecting optical system 7, arranged obliquely upward on one end side in the Y direction of the sample 1, includes: a condenser lens 8 for collimating the scattered/diffracted light R generated at a part where the laser beam L is irradiated; a slit member 9 in which an elongated slit 9a for limiting incident light to the scattered/diffracted light R is formed; a half mirror 10 for splitting the scattered/diffracted light R condensed by the condenser lens 8 into two optical paths; analyzers 11 and 12, each of which is an example of an optical unit inserted into each optical path; and a main detector 13 and a reference detector 14, each of which is formed of a photo multiplier tube (PMT) or the like and arranged at the end of each of the optical paths split by the half mirror. Further, the condenser lens 8 is arranged so as to focus on the sample 1 in almost every area of the scan line.

In the foreign matter inspection device configured in this manner, while the inspection stage St is moved linearly in the arrow X direction, the laser beam L from the laser oscillator 3 is irradiated from an oblique direction at a prescribed angle above the sample 1 while reciprocally and linearly scanning within a prescribed range in the Y direction, and the scattered/diffracted light R from the surface of the sample at this time is made incident to the optical detectors 13 and 14. In the present embodiment, the optical detector 13 is a main detector, and the optical detector 14 is a reference detector.

Figure 2:
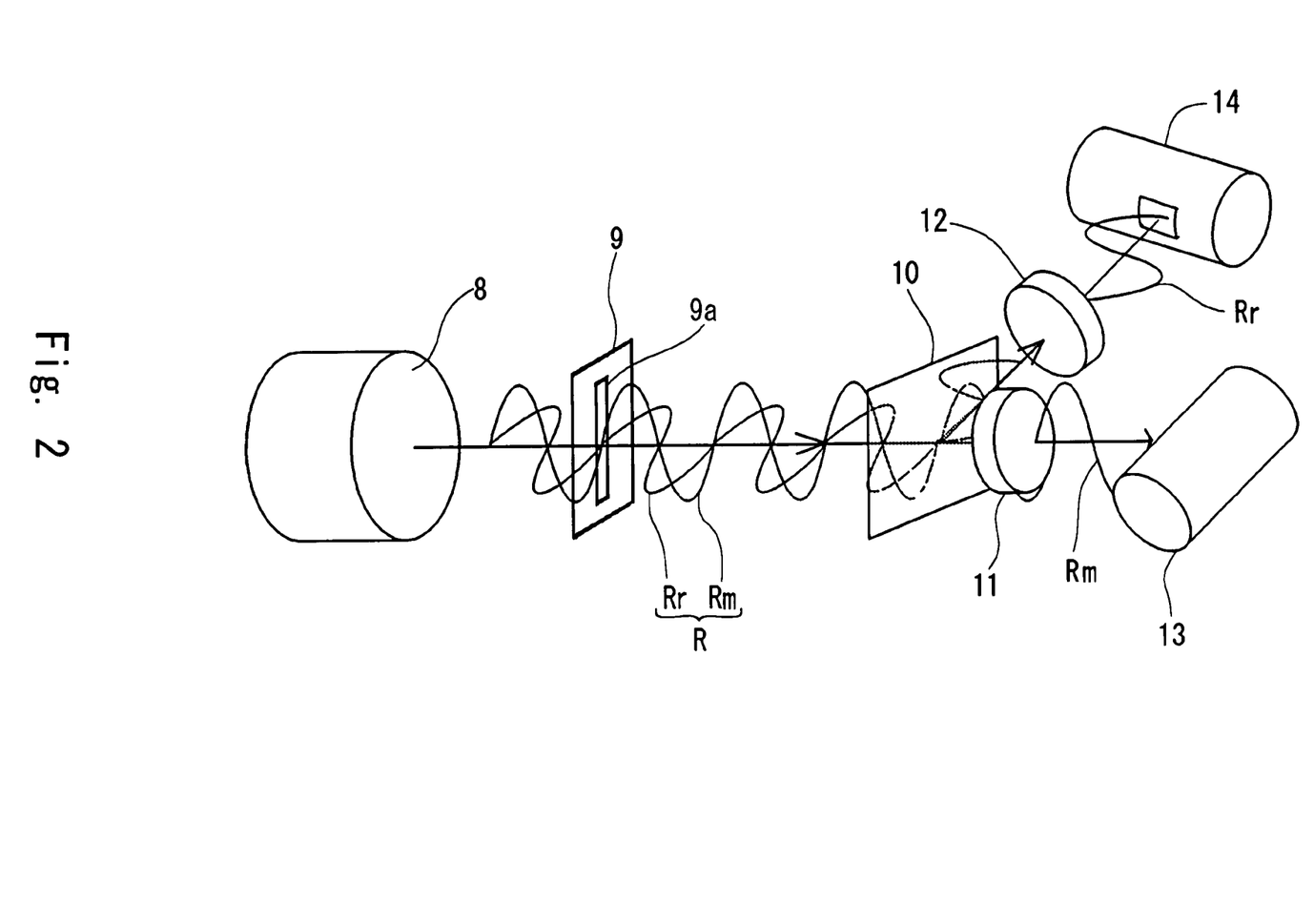
FIG. 2 is a diagram showing a part of the configuration of the substrate inspection device.

FIG. 2 is a diagram showing a configuration of a detecting optical system unit behind the half mirror 10. As shown in FIG. 2, the analyzer 11 placed before the main detector 13 is a polarization filter arranged at a specific polarization angle (for example, a polarization angle substantially perpendicular to the surface of the sample 1, hereinafter referred to as an M polarization angle) for extinguishing scattered light and diffracted light from the circuit pattern of the sample 1, and an analyzer 12 placed before the reference detector 14 is a polarization filter arranged at another polarization angle (for example, a polarization angle perpendicular to the M polarization angle, hereinafter referred to as an R polarization angle) for transmitting the scattered light and diffracted light from the circuit pattern on the sample 1.

Further, it is desirable that the foreign matter inspection device be so configured that the distance from the half mirror 10 to the main detector 13 and the distance from the half mirror 10 to the reference detector 14 are set to be the same distance so as to keep synchronism of signals detected by the main detector 13 and by the reference detector 14.

By using the foreign matter inspection device of the aforementioned configuration, it is possible to irradiate the laser beam L while scanning in the Y axis direction by the swing of galvanometer mirror 5. In such a state, by moving the stage St in the X direction at a constant speed v [mm/sec], it is possible to irradiate the laser beam L to cover the whole surface of the sample 1 to thereby obtain scattered/diffracted light R from the surface of each part of the sample 1. In the present embodiment, the condenser lens 8 and the slit member 9 are arranged such that an almost rectangle area 1a including an area where the light scans on the sample 1 and the slit 9a have a conjugate relationship while the condenser lens 8 is interposed therebetween. Thereby, it is possible to cut excess stray light and light caused by multiple diffractions and multiple scattering as much as possible. Further, since multiple diffractions and multiple scattering are caused not only on the surface of the sample 1 but also inside thereof, the surface on which the scattered/diffracted light R is generated includes the surface of the sample 1 and its periphery.

Then, the light is condensed by the condenser lens 8, and the scattered/diffracted light R passing through the slit 9a is split into two optical paths by the half mirror 10. The two analyzers 11 and 12 transmit the polarization components Rm and Rr of the M polarization angle and the R polarization angle, respectively, and the intensities of the polarization components Rm and Rr are detected by the detectors 13 and 14. That is, when an object that can scatter the laser beam L exists on the sample 1, signals are generated from respective detectors 13 and 14. In particular, the main detector 13 detects scattered/diffracted light caused by foreign matter in the state where scattered/diffracted light from a circuit pattern formed on the sample 1 is extinguished as much as possible, and the reference detector 14 detects the scattered/diffracted light from the circuit pattern formed on the sample 1 as intense as possible and also detects the scattered/diffracted light caused by the foreign matter.

Each of the detectors 13 and 14 of the present embodiment is formed of a PMT, and is capable of adjusting the sensitivity by the applied voltage. That is, the detecting sensitivity of the main detector 13 and the reference detector 14 can be adjusted independently, and also sensitivity adjustment can be carried out continuously without using an additional amplifier. Further, when a signal on the reference side is intense, the sensitivity of the reference detector 14 is adjusted such that a signal caused by a circuit pattern becomes almost the same as or a little lower than a signal caused by a circuit pattern detected by the main detector 13.

Figure 3:
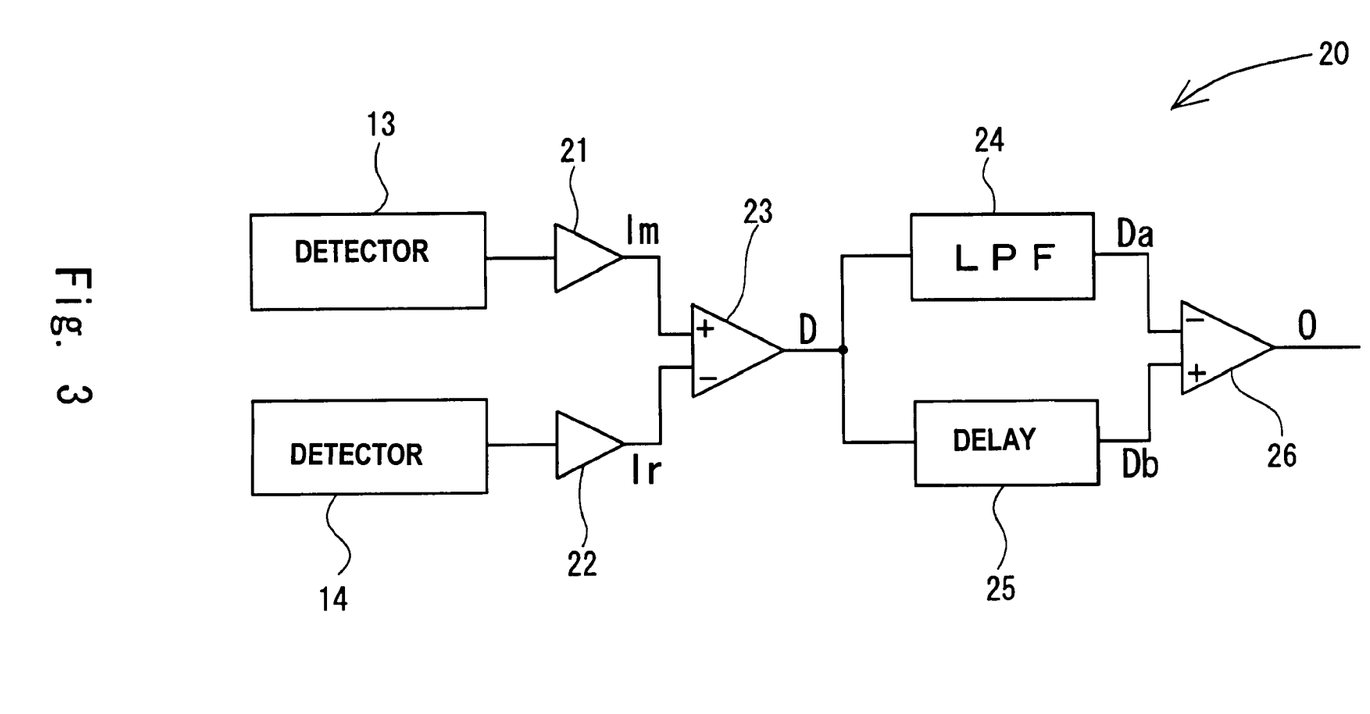
FIG. 3 is a diagram for explaining a configuration of a signal processor of the substrate inspection device.

FIG. 3 is a diagram showing a configuration of a signal processor for signals Im and Ir outputted from the respective detectors 13 and 14. As shown in FIG. 3, the signal processor 20 of the present embodiment includes: preamps 21 and 22 for amplifying outputs from the detectors 13 and 14; a subtracter 23 for calculating the difference between the amplified signals Im and Ir; a lowpass filter 24 whose cut off frequency $f_c$ is, for example, $d_m/v$ ($d_m$: Maximum of the diameter of foreign matter to be inspected) configured to transmit only frequencies lower than the prescribed frequency $f_c$ of the differential signal D calculated by the subtraction; a delay circuit 25 whose delay time is adjusted the same as one of the low pass filter for delaying the differential signal D by the same amount as the delay of the signal due to the lowpass filter 24; and a subtracter 26 for subtracting an output signal Da of the lowpass filter 24 from an output signal Db of the delay circuit 25 so as to obtain an output signal O.

Figure 4:
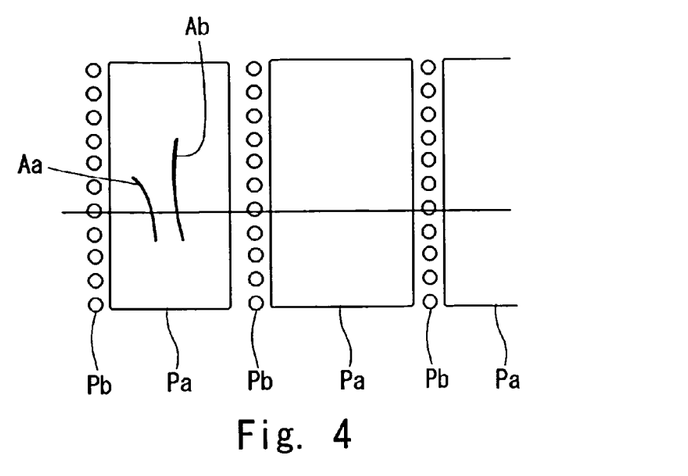
FIG. 4 is a diagram showing an exemplary inspection object substrate to be inspected.
Figure 5:
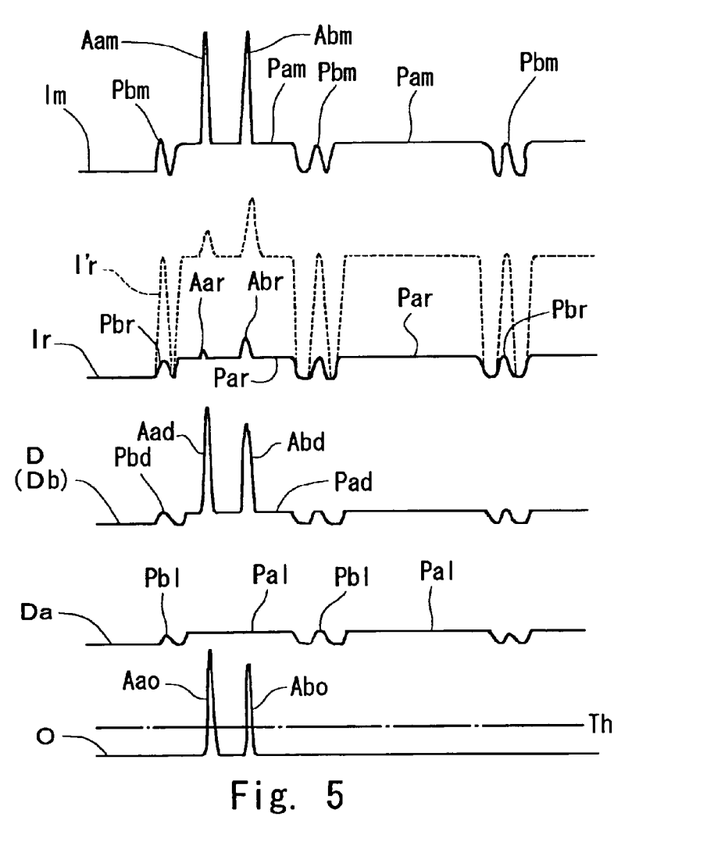
FIG. 5 is a diagram for explaining an example of a foreign matter inspecting method of the present invention.

FIG. 4 is a diagram showing an example of the sample 1 for explaining the operational effect by the foreign matter inspection device of the present embodiment, and FIG. 5 is a diagram for explaining signals Im and Ir detected when the sample 1 is measured, and for explaining a method of processing respective signals.

On the sample 1 shown in FIG. 4, there are formed circuit patterns Pa and circuit patterns Pb, arranged in a non-dense manner like as shown in FIG. 12B. The circuit pattern Pa has a relatively large area, and the circuit pattern Pb has a small area arranged between the circuit patterns Pa. Aa and Ab are foreign matter adhered on the surface part of the sample 1. In FIG. 5, a signal Ir' shown by a virtual line indicates an output signal of the reference detector 14 in the case where the signal is detected by the reference detector 14 with the same sensitivity as that of the main detector 13.

As shown in FIG. 5, the signal Im detected by the main detector 13 includes a substantially trapezoid signal Pam caused by the circuit pattern Pa whose width is narrower (shorter) than a series of m beam spots with diameter d and a somewhat acute peak signal Pbm caused by the circuit pattern Pb, and also includes an acute peak signal Aam caused by the foreign matter Aa and an acute peak signal Abm caused by the foreign matter Ab. The time interval T of scanning the dense pattern is represented by T=md/v, and the fundamental frequency is $$f_o\left(=\frac{1}{2T}\right).$$

Now, "m" is a number of beam spots, and "d" is a diameter of the beam spot (see FIG. 12(A)). Similarly, the signal Ir detected by the reference detector 14 includes a substantially trapezoid signal Par caused by the circuit pattern Pa and a somewhat acute peak signal Pbr caused by the circuit pattern Pb, and also includes an acute peak signal Aar caused by the foreign matter Aa and an acute peak signal Abr caused by the foreign matter Ab.

In the sample 1 shown in the present embodiment, multiple diffractions and multiple scattering are caused. Therefore, the signal Par caused by the circuit pattern Pa and the signal Pbr caused by the circuit pattern Pb in the signal Ir detected by the reference detector 14 are not sufficiently high compared with the signals Aar and Abr caused by the foreign matter Aa and Ab. Therefore, the amplification factor of the reference detector 14 is adjusted such that the signals Par and Pbr caused by the circuit patterns Pa and Pb included in the signal Ir become somewhat lower comparing with the signals Pam and Pbm caused by the circuit patterns Pa and Pb included in the signal Im, whereby the signals Aar and Abr caused by the foreign matter Aa and Ab included in the signal Ir are suppressed to low levels.

Accordingly, a difference signal D of the signals Im and Ir calculated by the subtracter 23 includes signals Pad and Pbd caused by the circuit patterns Pa and Pb as shown in FIG. 5. On the other hand, the signals Aad and Abd caused by the foreign matter Aa and Ab become higher signals comparing with the example explained by using FIG. 11. That is, it is desirable that the sensitivity (amplification factor) of the reference detector 14 be set to be small to the extent that the signals Aad and Abd, caused by the foreign matter Aa and Ab appeared in the difference signal D, are surely detected, that is, the sensitivity is at a level that the signals caused by the circuit patterns Pa and Pb are somewhat weaker than the signal Im detected by the main detector 13.

If all of the signals Aar, Abr and the like caused by the foreign matter included in the signal Ir are sufficiently smaller than the signals Par and Pbr caused by the circuit patterns, the amplification factor of the reference detector 14 may be adjusted such that the signals Par and Pbr have the same intensity as the signals Pam and Pbm included in the signal Im, whereby the signals Pad and Pbd caused by the circuit patterns Pa and Pb do not appear in the difference signal D.

Next, by transmitting the difference signal D through the lowpass filter 24 (see FIG. 3), the signals with acute peaks caused by the foreign matter Aa and Ab are removed, so that it is possible to transmit only signals $Pa_1$ and $Pb_1$ caused by the circuit patterns Pa and Pb. Here, since the signals Pad and Pbd caused by the circuit patterns Pa and Pb included in the difference signal D, obtained when the sample 1 causing multiple scattering and multiple diffractions is inspected, include multiple scattered light and multiple diffracted light on the surface part outside the focus of the laser beam L may be smoother when compared with a case where a sample not causing multiple scattering and multiple diffractions is inspected. Thus, in the case of the sample 1 causing multiple scattering and multiple diffractions, it is possible to discriminate the signals Pad and Pbd caused by the circuit patterns Pa and Pb by means of the lowpass filter 24.

On the other hand, if the difference signal D passes through the delay circuit 25, it is possible to delay the difference signal D by the similar amount to the case where it passes through the lowpass filter 24. In FIG. 5, in order to simplify the illustration, the difference signal D is shown such that it is same as an output signal Db of the delay circuit 25, disregarding the time delay.

Next, an output signal Da of the lowpass filter 24 is subtracted from the output signal Db of the delay circuit 25 by the subtracter 26, whereby the signals caused by the circuit patterns Pa and Pb are removed and the signal O only including signals Aao and Abo with acute peaks caused by the foreign matter Aa and Ab can be outputted. The obtained output signal O is compared with a prescribed threshold value Th, and those exceeding the threshold value Th can be detected as foreign matter signals.

Figure 6:
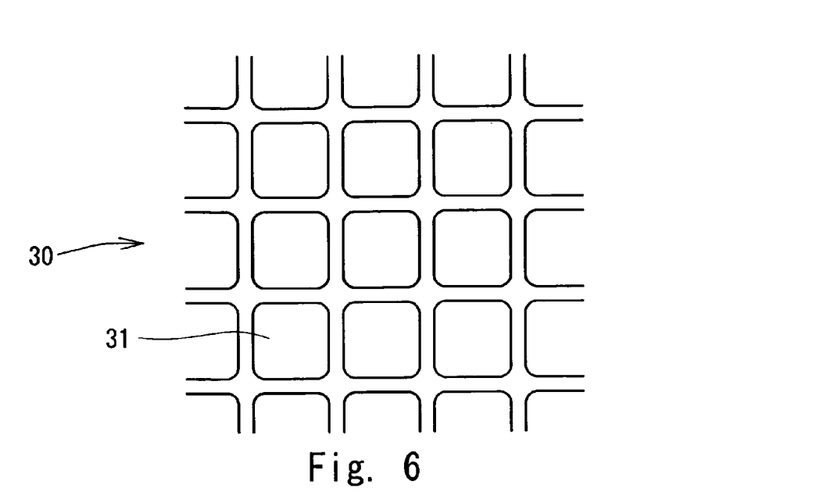
FIG. 6 is an illustration showing an exemplary inspection object substrate used as an experimentation for demonstrating the usability of the foreign matter inspection device and the foreign matter inspecting method of the present invention.
Figure 7:
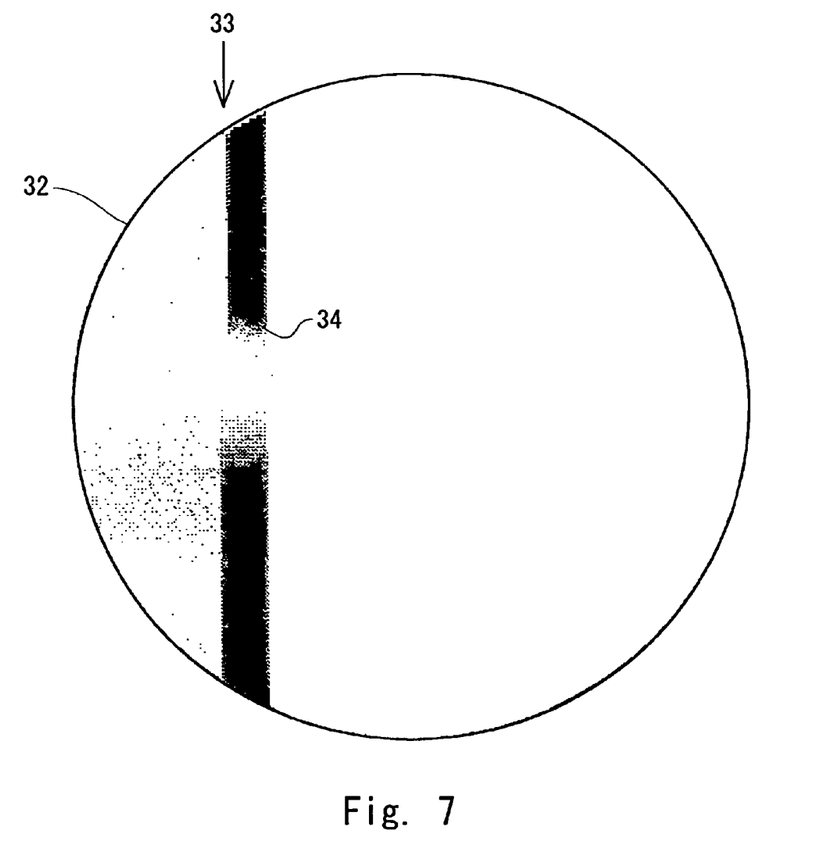
FIG. 7 is an illustration showing results of inspections, comparing a case of performing an inspection by using the inspection object substrate shown in FIG. 6 and the foreign matter inspecting method of the present invention with a case of not using the foreign matter inspecting method of the present invention.

FIG. 6 shows an exemplary inspection object substrate measured for demonstrating the operational effect of the foreign matter inspection device and the foreign matter inspecting method of the present invention. FIG. 7 shows the results obtained when the inspection object substrate is measured by the foreign matter inspecting method of the present invention and by the conventional method using a lowpass difference.

On an inspection object substrate 30 (sample) shown in FIG. 6, there are formed circuit patterns 31, each of which is in a substantially square shape of about 200 μm on a side and a corner of which is an arc of 50 μm radius, arranged vertically and horizontally. The sample 30 of this structure was inspected in the foreign matter inspection device explained in FIGS. 1 to 5, and at a certain point of time during the inspection, the output signal Ir from the reference detector 14 is inspected.

As shown in FIG. 7, the measured range of the inspection object was an area 32 having a diameter of dp [mm] (for example, 120 mm) of the sample 30, and inspection was performed scanning from the left to the right with velocity v [mm/sec] in the Figure. It was so set that when a position shown by the arrow 33 was inspected, the output signal Ir from the reference detector 14 was cut. A number of dots shown by the reference numeral 34 indicate foreign matter sensed by the foreign matter inspection apparatus. The reason why the foreign matter inspection was terminated is that the inspection was interrupted since there was too much foreign matter 34.

As is obvious from FIG. 7, in the sample 30 on which the relatively large circuit patterns 31 are formed, reflective light with intense and acute peak is generated at a corner or the like of the circuit pattern 31, whereby it is impossible to reduce false detection sufficiently because distinction between reflection and foreign matter cannot be made at corners of the circuit patterns by the conventional method using a lowpass difference. On the other hand, by the present invention, it is understood that false detection can be reduced effectively by using polarization difference with low pass difference method in combination.

Figure 8:
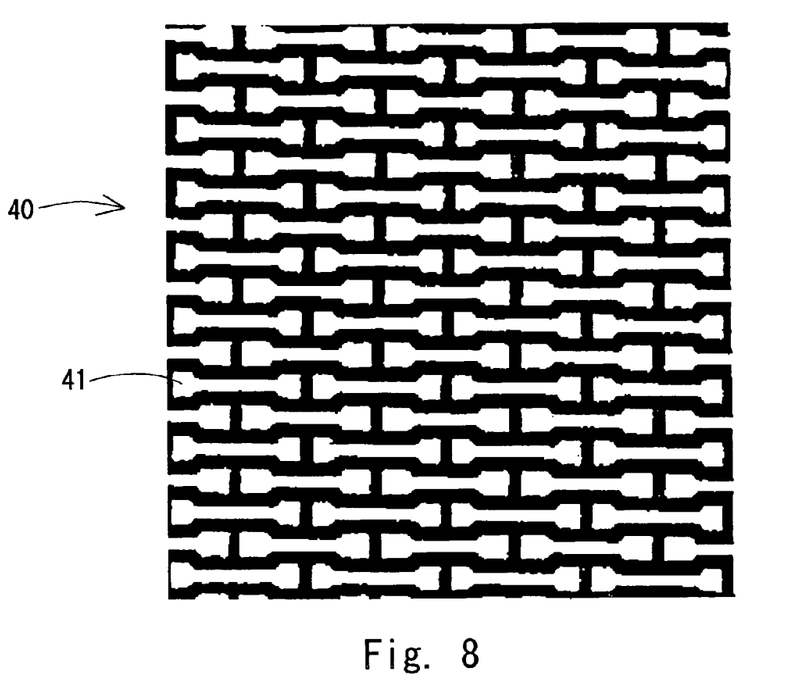
FIG. 8 is an illustration showing an example of an inspection object substrate used for another experimentation for demonstrating the usability of the foreign matter inspection device and the foreign matter inspecting method of the present invention.
Figure 9:
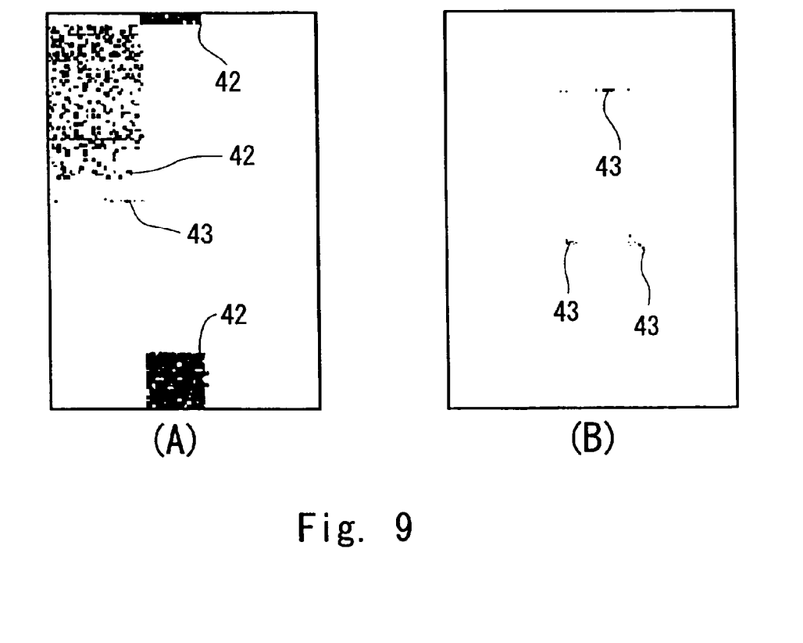
FIGS. 9(A) and 9(B) are illustrations showing results of inspections, comparing a case of performing an inspection by using the inspection object substrate showing in FIG. 8 and the foreign matter inspecting method of the present invention with a case of not using the foreign matter inspecting method of the present invention.

Next, FIG. 8 shows an example of another inspection object substrate measured for demonstrating the operational effect of the foreign matter inspection device and the foreign matter inspecting method of the present invention, and FIG. 9 shows results obtained when the inspection object substrate is measured by using the foreign matter inspecting method of the present invention and using the conventional polarization differential method.

On an inspection object substrate 40 (sample) shown in FIG. 8, a circuit pattern 41 having 1 μm width at the narrowest part is formed distributively in an area of 5 mm square. This sample 40 causes multiple scattering and multiple diffractions. FIG. 9(A) shows the result of inspecting the sample 40 by using the conventional polarization differential method, and FIG. 9(B) shows the result of inspection by using the foreign matter inspection device of the present invention. In FIGS. 9(A) and 9(B), reference numeral 42 indicates a circuit pattern detected as foreign matter and reference numeral 43 indicates detected foreign matter.

Comparing FIGS. 9(A) and 9(B), it is obvious that with the polarization differential method shown in FIG. 9(A), when the sensitivity is adjusted so as to be able to detect foreign matter on the sample 40 causing multiple scattering and multiple diffractions, the circuit pattern 41 is also detected as foreign matter, whereby it is difficult to confirm the position of the object foreign matter. On the other hand, by combining the polarization differential method and a method using a lowpass difference as shown in FIG. 9(B), it is possible to detect the foreign matter 43 in distinction from the circuit pattern 41.

What is claimed is:

1. A foreign matter inspection apparatus comprising:
a light source for irradiating, while scanning, a laser beam having a predetermined polarization angle to the surface of an inspection object substrate;
a main detector which includes a main optical unit for extinguishing scattered/diffracted light caused by a circuit pattern formed on the surface of the inspection object substrate among scattered/diffracted light generated on the surface of the inspection object substrate along with irradiation of the laser beam, and includes a first polarization member and detects an output signal from the main optical unit;
a reference detector which has a reference optical unit for transmitting scattered/diffracted light caused by the circuit pattern, and includes a second polarization member having a different polarization component than a first polarization component and detects an output signal from the reference optical unit; and
a signal processor for calculating a difference signal by subtracting the intensity of the polarization component detected by the reference detector from the intensity of the polarization component detected by the main detector, and obtaining a second difference signal between a first signal including a signal with a large width caused by the circuit pattern and a signal with an acute peak caused by foreign matter and a second signal that cuts off the signal with the acute peak with a filter, and comparing the value of the second difference signal with a threshold value to determine the presence of foreign matter.

2. The foreign matter inspection apparatus according to claim 1, further including a condenser lens for condensing the scattered/diffracted light, and a half mirror for splitting the scattered/diffracted light condensed by the condenser lens into two optical paths, the first polarization member and second polarization member are inserted in the respective optical paths, and the main detector and the reference detector are arranged at the ends of respective optical paths split by the half mirror.

3. A foreign matter inspection apparatus comprising:
a light source for irradiating, while scanning, a light beam having a predetermined polarization angle relative to the surface of an object substrate;
a main detector assembly removing scattered/diffracted light caused by a circuit pattern formed on the surface of the object substrate and providing a first output signal;
a reference detector assembly transmitting scattered/diffracted light caused by the circuit pattern and providing a second output signal; and
a signal processor means for calculating a difference signal by subtracting an intensity of a polarization component detected by the reference detector in the second output signal after adjusting an intensity of the reference detector assembly to a smaller level than an intensity of a polarization component detected by the main detector in the first output signal from the intensity in the first output signal, and obtaining a second difference signal between a first signal including a signal with a large width caused by the circuit pattern and a signal with an acute peak caused by foreign matter and a second signal that cuts off the signal with the acute peak with a filter, and comparing the value of the second difference signal with a threshold value to determine the presence of foreign matter.

4. The foreign matter inspection apparatus according to claim 3, further including a condenser lens for condensing the scattered/diffracted light; a half mirror for splitting the scattered/diffracted light condensed by the condenser lens into two optical paths; and analyzers inserted in the respective optical paths, and the main detector and the reference detector are arranged at the ends of respective optical paths split by the half mirror.

5. A foreign matter inspection method comprising the steps of:
irradiating, while scanning, a laser beam having a certain polarization angle to the surface of an inspection object substrate;
detecting a first output signal having a first polarization component of a first optical unit with a first polarization member for extinguishing scattered/diffracted light caused by a circuit pattern formed on the surface of the inspection object substrate among scattered/diffracted light generated on the surface of the inspection object substrate along with irradiation of the laser beam, and a second output signal having a second polarization component of a second optical unit with a second polarization member of a different polarization component than the first polarization member for transmitting the scattered/diffracted light caused by the circuit pattern;
calculating a difference signal by subtracting the second output signal of the second optical unit for transmitting the scattered/diffracted light caused by the circuit pattern from the first output signal of the first optical unit for extinguishing the scattered/diffracted light caused by the circuit pattern;
obtaining a second difference signal between a first signal including a signal with a large width caused by the circuit pattern and a signal with an acute peak caused by foreign matter and a second signal that cuts off the signal with the acute peak with a filter, and comparing the value of the second difference signal with a threshold value to determine the presence of foreign matter and a second signal with an acute peak caused by foreign matter, included in the difference signal, by their frequencies; and
comparing the first and second signals to determine the presence of foreign matter.

6. The foreign matter inspection method according to claim 5, further comprising the steps of condensing the scattered/diffracted light; splitting the condensed light into two optical paths by the half mirror; by arranging, to one of the split optical paths, an analyzer transmitting a polarization component of a polarization angle for extinguishing the scattered/diffracted light caused by the circuit pattern, detecting the intensity of the polarization component; and by arranging, to the other optical path, an analyzer transmitting a polarization component of a polarization angle for transmitting the scattered/diffracted light caused by the circuit pattern, detecting the intensity of the polarization component.

7. A foreign matter inspection apparatus characterized by comprising:
a light source for irradiating, while scanning, a laser beam having a predetermined polarization angle to the surface of an inspection object substrate;
a main detector which includes a main optical unit for extinguishing scattered/diffracted light caused by a circuit pattern formed on the surface of the inspection object substrate among scattered/diffracted light generated on the surface of the inspection object substrate along with irradiation of the laser beam, and detects an output signal from the main optical unit;
a reference detector which has a reference optical unit for transmitting scattered/diffracted light caused by the circuit pattern, and detects an output signal from the reference optical unit; and
a signal processor means for calculating a difference signal by adjusting the reference detector output to be smaller than the main detector output and comparing the intensity of a polarization component detected by the reference detector from the intensity of a polarization component detected by the main detector, discriminating a first signal with a large width caused by the circuit pattern and a second signal with an acute peak caused by foreign matter, included in the difference signal, by their frequencies and providing a discriminated signal to determine the presence of foreign matter.

8. The foreign matter inspection apparatus according to claim 7, further including a condenser lens for condensing the scattered/diffracted light; a half mirror for splitting the scattered/diffracted light condensed by the condenser lens into two optical paths; and analyzers inserted in the respective optical paths, and the main detector and the reference detector are arranged at the ends of respective optical paths split by the half mirror.

9. The foreign matter inspection apparatus according to claim 8 further including a slit member with a rectangular opening wherein the slit member provides a light scan area on the object substrate with the condenser lens positioned between the substrate and the slit member to enable a conjugate relationship to remove multiple diffractions and multiple scattering of light from the object substrate.

10. The foreign matter inspection apparatus according to claim 9 wherein the signal processor means includes a low pass filter and a delay circuit in parallel with the delay circuit matching the time delay of the low pass filter to process the difference signal.

11. The foreign matter inspection apparatus according to claim 10 wherein the low pass filter has a cut off frequency that is a function of maximum diameter of foreign matter to be detected on the object substrate.

12. The foreign matter inspection apparatus according to claim 11 wherein an output signal of the low pass filter is subtracted from an output of the delay circuit to remove any influence of a circuit pattern on the object substrate.

13. The foreign matter inspection apparatus according to claim 7 wherein the light source is a single laser oscillator emitting a laser beam of a predetermined polarization angle.

14. A foreign matter inspection method comprising the steps of:
irradiating, while scanning, a laser beam having a certain polarization angle to the surface of an inspection object substrate;
detecting a first output signal of a first optical unit having a first polarization component with a first polarization member for extinguishing scattered/diffracted light caused by a circuit pattern formed on the surface of the inspection object substrate among scattered/diffracted light generated on the surface of the inspection object substrate along with irradiation of the laser beam, and a second output signal having a second polarization component with a second polarization member of a second optical unit for transmitting the scattered/diffracted light caused by the circuit pattern;

calculating a difference signal by adjusting the second output to a smaller level than the first output and comparing the second output signal of the second optical unit for transmitting the scattered/diffracted light caused by the circuit pattern from the first output signal of the first optical unit for extinguishing the scattered/diffracted light caused by the circuit pattern;

discriminating with a low pass filter to provide a first signal with a large width caused by the circuit pattern and a second signal with an acute peak caused by foreign matter, included in the difference signal, by their frequencies;

comparing a signal including the first and second signal and the first signal to provide a third output signal; and measuring the third output signal with a threshold value to determine the presence of foreign matter.

15. The foreign matter inspection method according to claim 14, further comprising the steps of condensing the scattered/diffracted light; splitting the condensed light into two optical paths by the half mirror; by arranging, to one of the split optical paths, the first polarization member for transmitting a polarization component of a polarization angle for extinguishing the scattered/diffracted light caused by the circuit pattern, detecting the intensity of the polarization component; and by arranging, to the other optical path, the second polarization member for transmitting a polarization component of a polarization angle for transmitting the scattered/diffracted light caused by the circuit pattern, detecting the intensity of the polarization component.

* * * * *